United States Patent [19]

Yamauchi et al.

[11] Patent Number: 4,732,654
[45] Date of Patent: Mar. 22, 1988

[54] PREPARATION PROCESS OF INDOLE

[75] Inventors: Atsuyoshi Yamauchi, Naka; Seiya Iguchi, Tokyo; Yuzo Ono, Osaka; Hiroshi Kimura, Kamakura; Satoshi Morita, Yokosuka, all of Japan

[73] Assignee: Mitsui Toatsu Chemicals, Inc., Tokyo, Japan

[21] Appl. No.: 75,247

[22] Filed: Jul. 15, 1987

Related U.S. Application Data

[63] Continuation of Ser. No. 808,515, Dec. 13, 1985, abandoned.

[30] Foreign Application Priority Data

Dec. 26, 1984 [JP] Japan ................................. 59-272748

[51] Int. Cl.$^4$ ...................... B01D 3/14; C07D 209/04
[52] U.S. Cl. ........................................ 203/81; 203/71; 548/508
[58] Field of Search ....................... 203/73, 74, 81, 80, 203/77, 71; 548/508

[56] References Cited

U.S. PATENT DOCUMENTS

| 2,758,071 | 8/1956 | Biribauer | 203/77 |
| 2,953,575 | 9/1960 | Erner et al. | 548/508 |
| 4,032,411 | 6/1977 | Tornquist et al. | 203/14 |
| 4,404,063 | 9/1983 | Honda | 203/6 |
| 4,473,698 | 9/1984 | Matsuda et al. | 548/508 |
| 4,474,969 | 10/1984 | Honda et al. | 548/508 |

FOREIGN PATENT DOCUMENTS 2108496  5/1983  United Kingdom .

OTHER PUBLICATIONS

Patent Abstracts of Japan, C Field: (1) vol. 5, No. 106, Jul. 10, 1981, (2) vol. 7, No. 131, Jun. 8, 1983, (3) vol. 7, No. 209, Sep. 14, 1983.

Primary Examiner—Kenneth M. Schor
Attorney, Agent, or Firm—Fisher, Christen & Sabol

[57] ABSTRACT

In an industrial process for preparing indole by reacting aniline and ethylene glycol, high boiling-point impurities and non-volatile substances are removed in advance from the reaction mixture either before the recovery of aniline from the reaction mixture or before the subsequent rectification of the resultant indole. Indole of a high purity can thus be obtained.

4 Claims, No Drawings

PREPARATION PROCESS OF INDOLE

This application is a continuation of application Ser. No. 808,515 filed Dec. 13, 1985, and now abandoned.

BACKGROUND OF THE INVENTION (a) Field of the Invention

This invention relates to an improved process for the preparation of indole from aniline and ethylene glycol.

(b) Description of the Invention

Indole has found wide-spread commercial utility as a raw material for the chemical industry, for example, for perfumes and dyestuffs. Its application as a raw material for the synthesis of amino acids has attracted special attention in recent years. Indole has conventionally been prepared from expensive raw materials or through long and complicated preparation steps. As an economical process for preparing indole from inexpensive raw materials and through simpler steps, the vapor-phase catalytic reaction of aniline and ethylene glycol is known.

As catalysts useful for the above reaction, a variety of solid acid catalysts and metallic catalysts have been proposed. The principal reaction product of the vapor-phase catalytic reaction is of course indole. However, various compounds, in addition to indole, are also formed as a result of side reactions although their yields are not high. Moreover, it is also known that excess amounts of aniline in the reaction system are required to obtain indole with a good yield. When indole is industrially prepared in accordance with the above-mentioned process, it may not be possible to obtain it with sufficient purity as a raw material for the chemical industry unless a large amount of aniline which is contained in the resulting reaction mixture is separated and recovered for reutilization and unless the indole is purified by a suitable method such as distillation. Distillation is generally used as a method for effecting the separation and purification of indole on an industrial scale.

However, it is difficult to obtain indole with sufficient purity to permit its use as a raw material for the chemical industry if the recovery of the accompanying aniline and the purification of the indole are effected by ordinary distillation, because in ordinary distillation, aniline in an amount far greater than that expected from the gas-liquid equilibrium of aniline and indole is allowed to mix in the intended product, and the concentration of the thus-mixed aniline cannot be lowered even if the reflux ratio or theoretical plate number of a rectification column is increased.

SUMMARY OF THE INVENTION

An object of this invention is to provide an industrial process for the preparation of indole from aniline and ethylene glycol as raw materials.

Another object of this invention is to provide a method for separating and recovering aniline from a reaction mixture, which has been obtained by reacting aniline and ethylene glycol and then obtaining indole with a high purity.

These objects are achieved by the following process:

A process for preparing indole by reacting aniline and ethylene glycol in the presence of a catalyst, which comprises separating and removing high boiling-point impurities and non-volatile substances from the reaction mixture in advance either before the separation and recovery of aniline or before subsequent rectification of the resultant indole, followed by the subsequent rectification to obtain high-purity indole.

After aniline is separated and recovered by distillation from a reaction mixture, which has been obtained by the reaction of aniline and ethylene glycol, and the resultant indole fraction is rectified, aniline is still found in the resultant indole and hence lowers its purity. The present inventors have unexpectedly found that a most of the aniline which is mixed in the rectified indole, originates from high boiling-point impurities and non-volatile substances which remain in the bottom of a rectification column upon rectification of the indole. In other words, it has been found that the above-mentioned high boiling-point impurities and non-volatile substances, which are contained in the reaction mixture and are impurities that cannot be readily vaporized by the usual industrial distillation operations due to their low vapor pressures, are thermally decomposed into aniline under severe conditions for the rectification of indole. The thus-formed aniline is then allowed to mix in the rectified indole. It is therefore possible to obtain indole of good quality, the intended final product, when these high boiling-point impurities and non-volatile substances are separated and removed in advance either before the separation and recovery step of aniline from the reaction mixture or before the rectification step of the resultant indole. The rectification step of the resultant indole is then carried out.

DETAILED DESCRIPTION OF THE INVENTION

The present invention may be applied to a preparation process of indole, in which aniline and ethylene glycol are reacted in a vapor phase in the presence of a solid acid catalyst or a metallic catalyst. Among various catalysts useful in the practice of this invention, illustrative of solid acid catalysts may include:

(1) catalysts each containing the oxide or hydroxide [hereinafter called "catalyst material (1)"] of at least one element selected from Si, Al, B, Sb, Bi, Sn, Pb, Ga, Ti, Zr, Be, Mg, Y, Cu, Ag, Zn, Cd and the lanthanide elements, for example, CdO, ZnO, PbO$_2$, Al$_2$O$_3$—B$_2$O$_3$, SiO$_2$—ZnO, SiO$_2$—CaO, SiO$_2$—In$_2$O$_3$, SiO$_2$—SrO, SiO$_2$—CdO, SiO$_2$—Al$_2$O$_3$, SiO$_2$—MgO, TiO$_2$—SnO$_2$, TiO$_2$—ZrO$_2$, CdO$_2$—Bi$_2$O$_3$, SiO$_2$—Y$_2$O$_3$, SiO$_2$, Bi$_2$O$_3$—BeO, SiO$_2$—Ga$_2$O$_3$, SiO$_2$—La$_2$O$_3$, SiO$_2$—Ce$_2$O$_3$, SiO$_2$—ZnO—Ag$_2$O and SiO$_2$—MgO—CuO;

(2) catalysts each containing the sulfide or selenide [hereinafter called "catalyst material (2)"] of at least one element selected from Pd, Pt, Cr, Fe, Ni, Co, Zn, Mo, Cd and W, for example, PdS, PtS, CrS, FeS, NiS, CoS, ZnS, MoS$_2$, CdS, WS$_2$, ZnSe and CdSe; and (3) catalysts each containing an inorganic salt of at least one element selected from Fe, Tl, Ca, Mn, Bi, Sr, Y, Al, Zn, Cd, Ni, Mg, Sn, Be, Co and the lanthanide elements, i.e., at least one of their halides, carbonates, nitrates, sulfates, phosphates, pyrophosphates, phosphorus molybdates and silicotungstates [hereinafter called "catalyst materials (3)"], for example, ferric sulfate, thallium sulfate, calcium sulfate, manganese sulfate, bismuth sulfate, strontium sulfate, yttorium sulfate, cadmium bromide, aluminum sulfate, zinc sulfate, nickel sulfate, cadmium chloride, magnesium sulfate, indium sulfate, beryllium sulfate, cadmium nitrate, cobalt sulfate, zinc aluminum sulfate, magnesium chloride, cadmium sulfate and cadmium phosphate.

On the other hand, as exemplary metallic catalysts, may be mentioned catalysts each of which contains at least one element [hereinafter called "catalyst material (4)"] selected from Cu, Ag, Pt, Pd, Ni, Co, Fe, Ir, Os, Ru and Rh.

Among the above-described groups of catalyst materials, it is most preferable to use $SiO_2$—$ZnO$-$Ag_2O$ or $SiO_2$-$MgO$-$CuO$ in the group of catalyst materials (1), cadmium sulfide in the group of catalyst materials (2), cadmium sulfate in the group of catalyst materials (3), and Ag or Cu supported on a carrier having a large surface area in the group of catalyst materials (4).

These catalysts may be prepared by desirable processes or methods which are known per se in the art. The catalyst materials (1) may be prepared, for example, by hydrolyzing a water-soluble salt of the catalyst-forming element into its corresponding hydroxide and then drying and calcining the resultant gel or by thermally decomposing a readily-decomposable salt of the catalyst-forming element in air.

The catalyst materials (2) may be prepared, for example, by adding sodium sulfate or potassium selenide to a water-soluble salt of the catalyst-forming element or by bringing the catalyst-forming element or its salt into contact with hydrogen sulfide gas or hydrogen selenide gas.

Furthermore, the catalyst materials (4), which are metallic catalysts, may be prepared, for example, by reducing a salt of the catalyst-forming element or the hydroxide or oxide of the catalyst-forming element with a reducing agent such as hydrogen, formalin, formic acid, phosphorous acid or hydrazine.

These solid acid catalysts or metallic catalysts may be obtained by employing the above-described catalyst materials (1), (2), (3) and (4) either singly or in combination, which may optionally be supported on carriers. Any conventional carriers may be employed as such carriers. Usually, diatomaceous earth, pumice, titania, silica-alumina, alumina, magnesia, silica gel, activated carbon, activated clay, asbestos, among others, may be used. The above-mentioned catalyst materials may be supported on these carriers by the usual methods, resulting in carrier-supported catalysts.

No particular limitation is imposed on the amount of each of the above-mentioned catalyst materials to be supported on its associated carrier. Each of the above catalyst materials may be supported in an amount appropriate for its associated carrier, for example, in an amount of 1-50%.

In the indole preparation process of this invention, the reaction of aniline and ethylene glycol is carried out in a vapor phase in the presence of one of the above-described catalysts. The reactor may be a fixed-bed reactor, fluidized-bed reactor or moving-bed reactor.

Regarding aniline and ethylene glycol to be introduced into the reactor, ethylene glycol may range from 0.01 mole to 5 moles, preferably from 0.05 mole to 1 mole per mole of aniline.

The total amount of aniline and ethylene glycol which are introduced as raw materials may be within the range of from 0.01 to 10 g/hr.cc in terms of liquid hourly space velocity (LHSV). Prior to their introduction into the reactor, they are in advance caused to evaporate in an evaporator. Upon introduction, they may also be accompanied by, for example, steam, hydrogen, carbon monoxide, carbon dioxide, methane, nitrogen, neon or argon as a carrier gas. Of these carrier gases, steam, hydrogen and carbon monoxide are preferred because they are effective in prolonging the service life of the catalyst.

The reaction temperature may be within the range of 200°-600° C., preferably within the range of 250°-500° C.

As the reaction pressure, it is possible to choose any pressure ranging from atmospheric pressure to a pressure at which one or more components contained in either one of the raw materials or the reaction mixture form a condensed phase. From the practical viewpoint, the range of $1.1 \times 10^5$-$1.0 \times 10^7$ Pa is preferred, with the range of $2.0 \times 10^5$-$5.0 \times 10^6$ Pa being more preferred.

In the process of this invention, upon obtaining the intended final product by separating it from the reaction mixture of the above-described indole synthesis reaction in accordance with distillation, high boiling-point impurities and non-volatile substances are in advance removed by, for example, simple distillation prior to the rectification of the intended final product, whereby the purity of the intended final product is increased.

It is almost impossible to specify the high boiling-point impurities and non-volatile substances that are thermally decomposed to produce aniline. It is however known, for example, that ethylideneaniline readily dimerizes to form $\alpha,\gamma$-dianilino-$\alpha$-butylene, which in turn yields quinaldine when heated. In this case, it is possible that aniline is also formed stoichiometrically. It is thus possible that, under the reaction conditions, ethylene glycol, one of the raw materials, is dehydrated into acetaldehyde. This dehydration product may then be reacted with aniline to form ethylideneaniline, a Schiff base. The above-mentioned high boiling-point impurities and non-volatile substances are presumed to be ethylideneaniline.

In the present invention, the removal of the above-mentioned high boiling-point impurities and non-volatile substances may be conducted in an arbitrary order relative to the other steps such as the recovery step of unreacted aniline so long as it is effected prior to the rectification of the intended final product. Although the removal of the high boiling-point impurities and non-volatile substances may generally be effected by simple distillation or flash distillation, it may also be conducted by steam distillation, rectification or similar means. This removal operation may be carried out either batchwise or continuously without encountering any problem or inconvenience. There is no particular limitation imposed on the type of an evaporator which is to be employed for the removal of the high boiling-point impurities and non-volatile substances. The evaporator may hence be a jacket-type evaporator, falling-film evaporator, thermosiphon evaporator, kettle-shaped evaporator or forced-circulation evaporator. Its operation pressure may be suitably selected in view of the vapor pressures of the individual components to be processed, such as aniline and indole, and the temperature of the heating medium to be used. It may range from 0.1 to 760 mmHg, preferably from 1 to 100 mmHg.

According to the process of this invention, the high boiling-point impurities and non-volatile substances which remain in the rectification column and undergo gradual thermal decomposition to form aniline even after the completion of separation of unreacted aniline through distillation are separated and removed prior to the rectification of indole. Aniline is thus no longer allowed to mix in the indole fraction, leading to the provision of high-purity indole as the final product.

The process of this invention and its effects will hereinafter be described more specifically by the following Examples and Comparative Examples.

EXAMPLE 1

A tubular reactor having an inner diameter of 25 mm and made of stainless steel was packed with 500 cc of a catalyst having grain sizes of 3-4 mm for use in a reaction. The catalyst was obtained by press-forming cadmium sulfide powder. Under an elevated pressure of $8 \times 10^5$ Pa, hydrogen gas was fed at 2 l/min to the tubular reactor and the temperature of the catalyst layer was raised gradually from room temperature to 350° C., at which the catalyst layer was held. Thereafter, aniline and a 33% aqueous solution of ethylene glycol were mixed at 234 g/hr and 48 g/hr respectively, and the resultant mixture was vaporized. The vaporized mixture was fed to the tubular reactor to initiate their reaction. The off-gas of the tubular reactor was depressurized to atmospheric pressure and cooled to room temperature to obtain a condensate. The condensate was collected and allowed to separate into two phases. The organic phase was sampled for its quantitative analysis. The organic phase was found to contain 9.1% of indole.

The organic phase was then charged in a glassmade distillation apparatus which was composed of a still having an internal capacity of 2000 ml, a packed layer of 3 mm Dickson packing, said layer having an inner diameter of 35 mm and a height of 300 mm, a condenser and a splitter for refluxed liquid. Batchwise distillation was repeated at an operation pressure of 70 mmHg and a reflux ratio of 0.2 to recover aniline. The thus-obtained bottom contained 28.5% of aniline and 63.1% of indole.

After the recovery of aniline, 2050 g of the bottom was charged in a glass-made rotary evaporator and then subjected to simple distillation at an operation pressure of 5.0 mmHg and an oil bath temperature of 150° C. The evaporated components were caught in a condenser. The weight of the thus-obtained condensate was 1910 g. It contained 30.1% of aniline and 67.1% of indole.

The condensate was charged in the same distillation apparatus as that employed above for the recovery aniline, and was subjected to batchwise distillation at an operation pressure of 3.0 mmHg and a reflux ratio of 4.0 to obtain various fractions as given in Table 1. The indole fractions were so pure that their quality was sufficient as a raw material for the chemical industry.

TABLE 1

| Fraction No. | Weight (g) | Composition (wt. %) | | |
|---|---|---|---|---|
| | | Aniline | Indole | Others |
| 1 | 263 | 99.9 | trace | 0.1 |
| 2 | 198 | 99.7 | trace | 0.3 |
| 3 | 126 | 68.6 | 23.5 | 7.9 |
| 4 | 180 | 0.4 | 96.7 | 2.9 |
| 5 | 296 | trace | 99.3 | 0.7 |
| 6 | 346 | 0.0 | 99.7 | 0.3 |
| 7 | 401 | 0.0 | 98.5 | 1.5 |
| Bottom | 59 | 0.0 | 42.5 | 57.5 |
| Total | 1869 | 29.3 | 67.6 | 3.1 |

EXAMPLE 2

By using the bottom which had been obtained after the recovery of aniline in Example 1 as a feed material, a continuous operation was conducted in a wetted-wall falling-film evaporator having an inner diameter of 13 mm and a length of 515 mm and made of glass. The feed material was caused to flow down at 200 cc/hr along the inner wall of the falling-film evaporator. The temperature of its outer wall was heated at a constant level by means of a heating medium. The temperature of the heating medium was kept constant at 160° C. and the pressure was kept at 5 mmHg. The evaporated fractions were caught in a condenser. In a bottom obtained as a non-volatile fraction, indole was contained in an amount of 0.5% based on the indole fed as one of the raw materials. By using 2028 g of the thus-obtained condensate, the rectification of indole was conducted in the same manner as in Example 1. The resultant indole fractions were so pure that their quality was sufficient as a raw material for the chemical industry as shown in Table 2.

TABLE 2

| Fraction No. | Weight (g) | Composition (wt. %) | | |
|---|---|---|---|---|
| | | Aniline | Indole | Others |
| 1 | 303 | 99.9 | trace | 0.1 |
| 2 | 201 | 99.7 | trace | 0.3 |
| 3 | 159 | 55.0 | 36.8 | 8.2 |
| 4 | 191 | 0.1 | 95.4 | 4.5 |
| 5 | 315 | 0.0 | 99.3 | 0.7 |
| 6 | 431 | 0.0 | 99.8 | 0.2 |
| 7 | 329 | 0.0 | 98.4 | 1.6 |
| Bottom | 65 | 0.0 | 44.9 | 55.1 |
| Total | 2003 | 29.9 | 66.7 | 3.4 |

COMPARATIVE EXAMPLE 1

By using exactly the same distillation apparatus as that used in Example 1, a 2000 g portion of the bottom obtained after the recovery of aniline in Example 1 was subjected directly to batchwise distillation under exactly the same conditions as in Example 1 without separation and removal of its high boiling-point impurities and non-volatile substances.

The compositions of the thus-obtained fractions are given in Table 3. Each of the fractions contained aniline mixed therein to a substantial amount. It is especially noteworthy that aniline was also detected in the bottom although in a very small amount. This was most unusual, based on the vapor pressure of aniline. This appears to suggest that the aniline was formed as a result of thermal decomposition of high boiling-point impurities and non-volatile substances left in the still.

TABLE 3

| Fraction No. | Weight (g) | Composition (wt. %) | | |
|---|---|---|---|---|
| | | Aniline | Indole | Others |
| 1 | 296 | 99.9 | trace | 0.1 |
| 2 | 146 | 99.8 | trace | 0.2 |
| 3 | 166 | 54.3 | 39.6 | 6.1 |
| 4 | 210 | 4.1 | 94.3 | 1.6 |
| 5 | 276 | 1.3 | 98.1 | 0.6 |
| 6 | 370 | 0.7 | 98.5 | 0.8 |
| 7 | 324 | 0.4 | 97.9 | 1.7 |
| Bottom | 180 | 0.1 | 13.1 | 86.8 |
| Total | 1968 | 27.8 | 63.0 | 9.2 |

EXAMPLE 3

By using 500 cc of a pellet-like catalyst composed of a $SiO_2$ carrier of 3 mm in diameter and 2.5 mm in height and 1.5 wt.% of Cu supported on the $SiO_2$ carrier, a reaction was carried out in the same manner as in Example 1 to obtain an organic phase which contained 8.3% of indole.

Aniline was recovered from the organic phase in the same manner as in Example 1, thereby obtaining a bottom which contained 27.1% of aniline and 58.5% of indole.

Following the procedure of Example 1, 2010 g of the bottom was subjected to simple distillation to obtain 1760 g of condensate.

The condensate was distilled batchwise in the same manner as in Example 1 to obtain 962 g of an indole fraction which was equivalent to Fraction Nos. 5, 6 and 7. The purity of indole in the fraction was 99.2% and no aniline was detected.

COMPARATIVE EXAMPLE 2

A 1980 g portion of the bottom obtained after the recovery of aniline in Example 3 was subjected directly to batchwise distillation in the same manner as in Example 1 without separating high boiling-point impurities and non-volatile substances from the bottom, whereby 886 g of an indole fraction corresponding to Fraction Nos. 5, 6 and 7 was obtained. The purity of indole in the fraction was 98.1% and 0.9% of aniline was contained in the fraction.

EXAMPLE 4

By using 500 cc of a pellet-like catalyst composed of a $SiO_2$ carrier of 3 mm in diameter and 2.5 mm in height and 13 wt.% of Ag supported on the $SiO_2$ carrier, a reaction was carried out in the same manner as in Example 1 to obtain an organic phase which contained 9.0% of indole.

Aniline was recovered from the organic phase in the same manner as in Example 1, thereby obtaining a bottom which contained 29.5% of aniline and 66.8% of indole.

Following the procedure of Example 1, 2030 g of the bottom was subjected to simple distillation in a rotary evaporator to obtain 1890 g of condensate.

The condensate was distilled batchwise in the same manner as in Example 1 to obtain 1040 g of an indole fraction which was equivalent to Fraction Nos. 5, 6 and 7. The purity of indole in the fraction was 99.3% and no aniline was detected.

COMPARATIVE EXAMPLE 3

A 2010 g portion of the bottom obtained after the recovery of aniline in Example 4 was subjected directly to batchwise distillation in the same manner as in Example 1 without separating high boiling-point impurities and non-volatile substances from the bottom, whereby 970 g of an indole fraction corresponding to Fraction Nos. 5, 6 and 7 was obtained. The purity of indole in the fraction was 98.1% and 0.8% of aniline was contained in the fraction.

What is claimed is:

1. A process for preparing and highly purifying indole comprising reacting aniline and ethylene glycol in the vapor phase in the presence of a catalyst, said catalyst selected from the group consisting of a solid acid catalyst, a metallic catalyst and any combination thereof, at a temperature from 200° C. to 600° C. and a pressure from $1.1 \times 10^5$ Pa to $1.0 \times 10^7$ Pa, and then serially, distilling the thus-obtained reaction liquid in order to recover unreacted aniline as tops and in order to recover an indole-containing liquid as bottoms, separating and removing high-boiling point impurities and non-volatile substances from the indole-containing liquid by evaporation of the indole-containing component of the liquid and condensing the indole-containing component and rectifying the resulting indole-containing condensate in order to obtain high-purity indole containing substantially no aniline.

2. The process of claim 1 wherein the high-purity indole contains from about 95.4 to about 99.8 percent by weight indole and from 0.1 to essentially zero percent by weight aniline.

3. The process of claim 1 wherein the high-purity indole contains from about 98.5 to about 99.8 percent by weight indole and essentially zero percent by weight aniline.

4. The process of claim 1 wherein the high-purity indole contains from about 99.2 to about 99.8 percent by weight and from a trace to essentially zero percent by weight aniline.

* * * * *